United States Patent [19]

Martel et al.

[11] 4,257,978
[45] Mar. 24, 1981

[54] NOVEL POLYHALOGENATED CYCLOPROPANE CARBOXYLIC ACID DERIVATIVES

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 51,348

[22] Filed: Jun. 25, 1979

Related U.S. Application Data

[62] Division of Ser. No. 834,573, Sep. 19, 1977, Pat. No. 4,179,575.

[30] Foreign Application Priority Data

Sep. 21, 1976 [FR] France ................................. 76 28279
Jul. 19, 1977 [FR] France ................................. 77 22078

[51] Int. Cl.³ ............................................. C07C 53/50
[52] U.S. Cl. ................................................. 260/544 L
[58] Field of Search ............................. 260/544 L, 546; 560/124

[56] References Cited

FOREIGN PATENT DOCUMENTS 2621833 11/1976 Fed. Rep. of Germany ............ 562/506
2805312  8/1978 Fed. Rep. of Germany ............ 560/124

OTHER PUBLICATIONS

Matsuo, Takashi et al., Chemical Abstracts 86 (1977), #89,254g.

*Primary Examiner*—Natalie Trousof
*Assistant Examiner*—L. Hendriksen
*Attorney, Agent, or Firm*—Hammond & Littell, Weissenberger and Muserlian

[57] ABSTRACT

Novel polyhalogenated cyclopropane carboxylic acid compounds of the formula

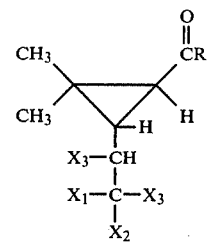

wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is selected from the group consisting of hydroxy, halogen, alkoxy of 1 to 7 carbon atoms or R represents OM group wherein M is selected from the group consisting of metal, organic base, acyl of an organic carboxylic acid and an acyl of the said acid in any of the possible isomer forms which are useful as intermediates for the production of pesticidal eaters thereof and which also possess antifungal and biocidal activity.

8 Claims, No Drawings

NOVEL POLYHALOGENATED CYCLOPROPANE CARBOXYLIC ACID DERIVATIVES

PRIOR APPLICATION

This application is a division of our copending application Ser. No. 834,573 filed Sept. 19, 1977, now U.S. Pat. No. 4,179,575.

OBJECTS OF THE INVENTION

It is an object of the invention to provide the novel cyclopropane carboxylic acids and their functional derivatives of formula I and a process for their preparation.

It is another object of the invention to provide novel antifungal and biocidal compositions and to provide a novel method of combatting fungi and bacteria.

These and other objects and advantages of the invention will become obvious from the following detailed description.

THE INVENTION

The novel polyhalogenated cyclopropane carboxylic acid compounds of the invention have the formula

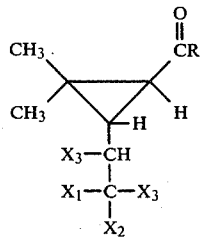

wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is selected from the group consisting of hydroxy, halogen, alkoxy of 1 to 7 carbon atoms or R represents OM group wherein M is selected from the group consisting of metal, organic base, acyl of an organic carboxylic acid and an acyl of the said acid in any of the possible isomer forms.

The cyclopropane carboxylic acids of formula I exist in numerous isomeric forms since they generally have 3 asymmetric carbon atoms, namely the 1- and 3-carbon atoms of the cyclopropane ring and the 1'-carbon atom of polyhalogenated ethyl fixed in the 3-position of the cyclopropane ring. When the three $X_1$, $X_2$ and $X_3$ substituents are all different from each other, an additional asymmetric carbon atom exists in the 2'-position of the 3-polyhalogenated ethyl group. The two diasteroisomeric forms of the acids of formula I due to the existence of the asymmetric carbon atoms in the 1'-position can exist and are effectively characterized by their RMN Spectrum or by their rate of migration in thin-layer chromatography and the two diasteroisomers are indicated as the A and B isomers.

Among the preferred compounds of formula I are those wherein $X_1$ and $X_2$ are identical and those wherein $X_1$ and $X_2$ are different.

Among the preferred carboxylic acids K of the invention of formula I are 2,2-dimethyl-3-(1',2'-dichloro-2',2'-dibromoethyl)-cyclopropane-1-carboxylic acids, 2,2-dimethyl-3-(1',2',2',2'-tetrachloroethyl)-cyclopropane-1-carboxylic acids, 2,2-dimethyl-3-(1',2'-dichloro-2',2'-difluoroethyl)-cyclopropane-1-carboxylic acids, 2,2-dimethyl-3-(1',2'-dibromo-2',2'-dichloroethyl)-cyclopropane-1-carboxylic acids, 2,2-dimethyl-3-(1',2'-dibromo-2',2'-difluoroethyl)-cyclopropane-1-carboxylic acids, 2,2-dimethyl-3-(1',2',2',2'-tetrabromoethyl)-cyclopropane-1-carboxylic acids, 2,2-dimethyl-3-(1',2'-diiodo-2',2'-difluoroethyl)-cyclopropane-1-carboxylic acids, 2,2-dimethyl-3-(1',2'-diiodo-2',2'-dichloroethyl)-cyclopropane-1-carboxylic acids, 2,2-dimethyl-3-(1',2'-diiodo-2,2-dibromoethyl)-cyclopropane-1-carboxylic acids, 2,2-dimethyl-3-(1',2',2'-tribromoethyl)-cyclopropane-1-carboxylic acids, 2,2-dimethyl-3-(1',2'-dichloro-2'-bromoethyl)-cyclopropane-1-carboxylic acids, 2,2-dimethyl-3-(1',2',2'-trichloroethyl)-cyclopropane-1-carboxylic acids, 2,2-dimethyl-3-(1',2'-dibromo-2'-chloroethyl)-cyclopropane-1-carboxylic acids, 2,2-dimethyl-3-(1',2'-dichloro-2'-fluoroethyl)-cyclopropane-1-carboxylic acids, 2,2-dimethyl-3-(1',2'-dibromo-2'-fluoroethyl)-cyclopropane-1-carboxylic acids, 2,2-dimethyl-3-(1',2'-diiodo-2'-fluoroethyl)-cyclopropane-1-carboxylic acids, 2,2-dimethyl-3-(1',2'-diiodo-2'-chloroethyl)-cyclopropane-1-carboxylic acids, 2,2-dimethyl-3-(1',2'-diiodo-2'-bromoethyl)-cyclopropane-1-carboxylic acids, 2,2-dimethyl-3'(1',2',2'-trichloro-2'-fluoroethyl)-cyclopropane-1-carboxylic acids, 2,2-dimethyl-3-(1',2'-dibromo-2'-chloro-2'-fluoroethyl)-cyclopropane-1-carboxylic acids, 2,2-dimethyl-3-(1',2',2'-trichloro-2'-bromoethyl)-cyclopropane-1-carboxylic acids, 2,2-dimethyl-3-(1',2',2'-tribromo-2'-chloroethyl)-cyclopropane-1-carboxylic acids, 2,2-dimethyl-3-(1',2',2'-tribromo-2'-fluoroethyl)-cyclopropane-1-carboxylic acids, 2,2-dimethyl-3-(1',2'-dichloro-2'-bromo-2'-fluoroethyl)-cyclopropane-1-carboxylic acids, 2,2-dimethyl-3-(1',2'-diiodo-2'-chloro-2'-fluoroethyl)-cyclopropane-1-carboxylic acids, 2,2-dimethyl-3-(1',2'-diiodo-2'-bromo-2'-fluoroethyl)-cyclopropane-1-carboxylic acids and 2,2-dimethyl-3-(1',2'-diiodo-2'-bromo-2'-chloroethyl)-cyclopropane-1-carboxylic acids.

It is to be understood that the acids of formula I may be prepared as cyclopropane carboxylic acids of (1S,cis) or (1S, trans) structure as well as dl cis [equimolar mixture of (1R, cis) and (1S, cis)] or dl trans [equimolar mixture of (1R, trans) and (1S, trans)] or mixtures of acids of dl-cis and dl-trans structure. Preferably, the compounds are cyclopropane carboxylic acids of (1R, cis) or (1R, trans) structure as well as acids of dl-cis or dl-trans structure.

Examples of specific acids in the form of their A or B isomers or mixtures thereof are 2,2-dimethyl-3R-(1',2',2',2'-tetrabromoethyl)-cyclopropane-1R-carboxylic acid, 2,2-dimethyl-3S-(1',2',2',2'-tetrabromoethyl)-cyclopropane-1R-carboxylic acid, 2,2-dimethyl-3S-(1',2'-dibromo-2',2'-dichloroethyl)-cyclopropane-1R-carboxylic acid, 2,2-dimethyl-3R-(1',2'-dichloro-2',2'-dibromoethyl)-cyclopropane-1R-carboxylic acid, 2,2-dimethyl-3S-(1',2'-dichloro-2',2'-dibromoethyl)-cyclopropane-1R-carboxylic acid, 2,2-dimethyl-3S-(1',2'-dibromo-2',2'-difluoroethyl)-cyclopropane-1R-carboxylic acid, 2,2-dimethyl-3R(1',2'-dibromo-2',2'-dichloroethyl)-cyclopropane-1R-carboxylic acid, 2,2-dimethyl-3R-(1',2',2',2'-tetrachloroethyl)-cyclopropane-1R-carboxylic acid and 2,2-dimethyl-3S-(1',2',2',2'-tetrachloroethyl)-cyclopropane-1R-carboxylic acid as well as 2,2-dimethyl-3R-(1',2'-dibromo-2',2'-difluoroethyl)-cyclopropane-1R-carboxylic acid and 2,2-dimethyl-3R-(1',2'-dibromo-2'-(R,S)-fluoro-2'-chloroethyl)-cyclopropane-1R-carboxylic acid.

The novel process of the invention for the preparation of the acids of formula I comprises reacting an acid of the formula

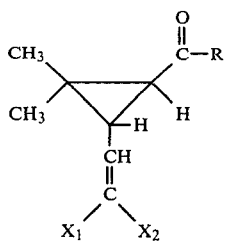

wherein R, $X_1$ and $X_2$ have the above definition or a functional derivative which may be in any isomer form with a chlorination, bromination or iodation agent capable of adding the said halogen across the double bond of the side chain of the cyclopropane carboxylic acid.

The halogenation agent is preferably chlorine, bromine or iodine and the reaction is preferably effected in an organic solvent not affected by the halogenating agent such as acetic acid, methylene chloride, carbon tetrachloride or chloroform.

The functional derivatives of the acids may be the halide such as acid chloride or the acid anhydride or mixed acid anhydride, an alkyl ester of 1 to 7 carbon atoms, a metal salt such as alkali metal and alkaline earth metals, ammonium salt or salt of an organic base such as tertiary amines which may be prepared by known methods.

The novel antifungal compositions of the invention are comprised of an antifungally effective amount of at least one cyclopropane carboxylic acid of formula I wherein R is hydroxyl and an inert carrier. The compositions may contain one or more other pesticides and may be in the form of powders, granules, suspensions, emulsions, solutions, or other classical preparations prepared in the usual fashion.

The compositions usually contain a vehicle and/or a non-ionic surface active agent to ensure a uniform dispersion of the ingredients of the mixture. The vehicle may be a liquid such as water, alcohol, hydrocarbons or other organic solvents or a mineral, animal or vegetable oil or a powder such as talc, clays, silicates or kieselguhr. When the compositions are powders for spraying, they preferably contain 25 to 95% by weight of the active material and 2.5 to 95% by weight when used as a foliar powder and for sprayable powders or liquids, to spray on the soil, they are preferably containing 10 to 30% by weight of the active material.

The compositions have good antifungal properties which make them useful to combat fungi, particularly parasitic fungi in crops such as diverse parasitic fungi in tomatos, cucumbers and grape vines. Tests have shown the compositions to be effective against Botrytis, Fusarium, Phoma and Penicillium fungi.

The novel method of the invention of combatting fungi comprises contacting fungi with an antifungally effective amount of at least one compound of formula I wherein R is hydroxyl.

The novel biocidal compositions of the invention comprise a biocidally effective amount of at least one compound of formula I wherein R is hydroxyl and an inert carrier. The compositions may contain one or more other pesticides and may be in the form of powders, granules, suspensions, emulsions, solutions or other classical preparation prepared in the ususal fashion.

The compositions usually contain a vehicle and/or a non-ionic surface active agent to ensure a uniform dispersion of the ingredients of the mixture. The vehicle may be a liquid such as water, alcohol, hydrocarbons or other organic solvents or a mineral, animal or vegetable oil or a powder such as talc, clays, silicates or kieselguhr. The compositions preferably contain 20 to 95% by weight of the active ingredient.

The biocidal compositions of the invention have good bactericidal properties and are therefore useful as industrial biocides and have been shown to be useful as elevated biocides in industrial media. Tests have shown them effective in glues and for industrial charges of the Kaolin slurry type infested with a complex mixture of bacteria which usually develope in industrial substrates. They are useful for protecting glue, industrial charges and cutting oils as well as for preventing and eliminating formation of microbial slimes in paper circuits or for treatment of hides, tanning liquors and leather.

The novel biocidal method of the invention comprises contacting bacteria with a biocidally effective amount of at least one compound of formula I wherein R is hydroxyl.

The compounds of formula I are also useful as intermediates for the preparation of esters of the said carboxylic acids when R is hydroxyl as described in commonly assigned U.S. patent application Ser. No. 834,659 filed on even date herewith which esters possess pesticidal properties such as insecticidal, acaricidal, nematocidal and antifungal activity.

In the following examples there are described several preferred embodiments to illustrate the invention. However, it should be understood that the invention is not intended to be limited to the specific embodiments.

EXAMPLE 1

2,2-dimethyl-3R-(1',2',2',2'-tetrabromoethyl)-cyclopropane-1R-carboxylic acid

A solution of 10.4 g of bromine in 22 ml of carbon tetrachloride was added to a mixture of 19.4 g of 2,2-dimethyl-3R-(2',2'-dibromovinyl)-cyclopropane-1R-carboxylic acid in 150 ml of carbon tetrachloride and the mixture was stirred at 20° C. for one hour and was evaporated to dryness under reduced pressure. The 31.4 g of raw product with a melting point of 145° C. was crystallized from 110 ml of carbon tetrachloride to obtain 22.12 g of 2,2-dimethyl-3R-(1',2',2',2'-tetrabromoethyl)-cyclopropane-1R-carboxylic acid melting at 150° C.

The product was determined by RMN spectrum to be a mixture of A and B isomers which was revealed to be one compound (corresponding to about ⅔ of the mixture) presenting peaks at 1.31–1.43 ppm corresponding to hydrogens of geminal methyl groups and at 5.33–5.66 ppm corresponding to hydrogen fixed on an asymetrical monobrominated carbon and a second compound (about ⅓ of the mixture) presenting peaks at 1.28–1.48 ppm corresponding to hydrogens of geminal methyl groups and at 4.24–5.34 ppm corresponding to hydrogen fixed on an asymetrical monobrominated carbon. In the mixture, there were also peaks at 1.67–2.17 ppm (hydrogens at 1- and 3-positions of cyclopropane) and toward 11.25 ppm (mobile hydrogen of carboxylic group).

Analysis: $C_8H_{10}Br_4O_2$; molecular weight=457.804

Calculated: %C 20.99; %H 2.20; %Br 69.82; Found: 20.9; 2.2; 70.2.

STEP A:

2,2-dimethyl-3R-(1',2',2',2'-tetrabromoethyl)-cyclopropane-1R-carboxylic acid chloride 8.5 ml of thionyl chloride were added to a mixture of 179 ml of petroleum ether (b.p. 35°–75° C.) and 0.2 ml of dimethylformamide and after heating the mixture to reflux, a mixture of 35.76 g of the above acid in 150 ml of methylene chloride was added thereto. The mixture was stirred at reflux for 2 hours and was then cooled and evaporated to dryness. The residue was taken up in toluene and the solution was evaporated to dryness under reduced pressure to obtain 38 g of raw 2,2-dimethyl-3R-(1',2',2',2'-tetrabromoethyl)-cyclopropane-1R-carboxylic acid chloride melting at 88° C. which was used as is for the next step.

STEP B: (S) α-cyano-3-phenoxy-benzyl 2,2-dimethyl-3R-(1',2',2',2'-tetrabromoethyl)-cyclopropane-1R-carboxylate 7.5 ml of pyridine were added to a solution of 18.4 g of (S) α-cyano-3-phenoxy-benzyl alcohol in 100 ml of benzene and then 38 g of the raw product of Step A were added thereto at 10° C. under an inert atmosphere. The mixture was stirred at 20° C. for 15 hours and water was added thereto with stirring. The organic phase was decanted and the aqueous phase was extracted with benzene. The combined benzene phases was washed successively with water, sodium bicarbonate solution and then water, N hydrochloric acid and finally with water. The benzene phase was dried and evaporated to dryness under reduced pressure. The residue was chromatographed over silica gel and was eluted to obtain a mixture of the A and B isomers of (S) α-cyano-3-phenoxy-benzyl 2,2-dimethyl-3R-(1',2',2',2'-tetrabromoethyl)-cyclopropane-1R-carboxylate.

EXAMPLE 2

2,2-dimethyl-3S-(1',2',2',2'-tetrabromoethyl)-cyclopropane-1R-carboxylic acid

Using the procedure of Example 1, 2,2-dimethyl-3S-(2',2'-dibromovinyl)-cyclopropane-1R-carboxylic acid was brominated to form a mixture of the A and B isomers of 2,2-dimethyl-3S-(1',2',2',2'-tetrabromoethyl)-cyclopropane-1R-carboxylic acid.

RMN Spectrum (deuterochloroform):
peaks at 1.30 to 1.40 ppm (hydrogens of 2-methyls of cyclopropane); at 1.65–1.74 and 1.97 to 2.37 ppm (1- and 3-hydrogens of cyclopropane); at 4.30–4.47 and 4.47–4.65 ppm (1'-hydrogen of 3-ethyl of cyclopropane); and at 9.63 ppm (carboxyl hydrogen).

(S) 1-oxo-2-allyl-3-methyl-cyclopent-2-en-4-yl 2,2-dimethyl-3S-(1',2',2',2'-tetrabromoethyl)-cyclopropane-1R-carboxylate Using the procedure of Example 1, the above acid was reacted with thionyl chloride to form 2,2-dimethyl-3S-(1',2',2',2'-tetrabromoethyl)-cyclopropane-1R-carboxylic acid chloride which was then reacted with (S) allethrolone in the presence of pyridine to form the A and B isomers of (S) allethrolone 2,2-dimethyl-3S-(1',2',2',2'-tetrabromoethyl)-cyclopropane-1R-carboxylate.

I.R. Spectrum (chloroform):

Absorptions at 1725, 1710, 1655, 1638, 995 and 918 cm$^{-1}$

RMN Spectrum (deuterochloroform):
peaks at 1.30–1.32–1.36 ppm (hydrogens of 2-methyls of cyclopropane); at 1.98–2.05 ppm (hydrogens of 3-methyl of allethrolone); at 4.83–5.25 ppm (hydrogens of terminal methylene of allyl of allethrolone); at 4.30–4.48 and 4.48–4.67 ppm (1'-hydrogen of 3-ethyl of cyclopropane); and at 5.33–6.17 ppm (2'-hydrogens of allyl of allethrolone).

EXAMPLE 3

2,2-dimethyl-3S-(1',2'-dibromo-2',2'-dichloroethyl)-cyclopropane-1R-carboxylic acid Using the procedure of Example 1, 2,2-dimethyl-3S-(2',2'-dichlorovinyl)-cyclopropane-1R-carboxylic acid was reacted with bromine to obtain a mixture of the A and B isomers of 2,2-dimethyl-3S-(1',2'-dibromo-2,2-dichloroethyl)-cyclopropane-1R-carboxylic acid.

RMN Spectrum (deuterochloroform):
peaks at 1.17–1.37 ppm (hydrogens of 2-methyls of cyclopropane); at 1.65–1.73 and 1.93–2.03 ppm (hydrogens in 1-position of cyclopropane); and at 4.23–4.45 and 4.45–4.62 ppm (1'-hydrogen of 3-ethyl of cyclopropane).

(S) allethrolone 2,2-dimethyl-3S-(1',2'-dibromo-2',2'-dichloroethyl)-cyclopropane-1R-carboxylate Using the procedure of Example 1, the above acid was reacted with thionyl chloride to obtain 2,2-dimethyl-3S-(1',2'-dibromo-2',2'-dichloroethyl)-cyclopropane-1R-carboxylic acid chloride with an IR spectrum in chloroform of absorption at 1777 cm$^{-1}$. The said product was then reacted with (S) allethrolone in the presence of pyridine to obtain a mixture of the A and B isomers of (S) allethrolone 2,2-dimethyl-3S-(1',2'-dibromo-2',2'-dichloroethyl)-cyclopropane-1R-carboxylate.

RMN Spectrum (deuterochloroform):
peaks at 1.30 to 1.34 ppm (hydrogens of 2-methyls of cyclopropane); at 1.63 to 3.0 ppm (1- and 3-hydrogens of cyclopropane); at 2.05 ppm (hydrogens of 3-methyl of cyclopropane); at 1.95–3.03 ppm (hydrogens of 1'-methylene of allyl); at 4.25–4.43–4.61 ppm (1'-hydrogen of 3-ethyl of cyclopropane); at 4.25 ppm (hydrogens of terminal methylene of allyl); at 4.83 to 5.41 ppm (2'-hydrogen of allyl); and at 5.83 ppm (4-hydrogens of allethrolone).

EXAMPLE 4

2,2-dimethyl-3R-(1',2'-dichloro-2',2'-dibromoethyl)-cyclopropane-1R-carboxylic acid 11.8 g of chlorine were bubbled into 30 ml of carbon tetrachloride at −15° C. and then a solution of 24 g of 2,2-dimethyl-3R-(2',2'-dibromovinyl)-cyclopropane-1R-carboxylic acid in 37 ml of carbon tetrachloride was slowly added thereto at −10° C. The mixture was stirred for 90 minutes at 0° C. and 2 hours at 25° C. and was then evaporated to dryness under reduced pressure. The residue was crystallized from carbon tetrachloride to obtain 7.4 g of the A and B isomers of 2,2-dimethyl-3R-(1',2'-dichloro-2',2'-dibromoethyl)-cyclopropane-1R-carboxylate melting point of 134° C.

RMN Spectrum:
peaks at 1.32–1.44 ppm and at 1.28–1.48 ppm (hydrogens of 2-methyls of cyclopropane); at 5.08–5.45 and 4.67–5.0 ppm (1'-hydrogen of 3-ethyl of cyclopropane); and at 10.1 ppm (carboxyl hydrogen).

(R,S)α-cyano-3-phenoxy-benzyl 2,2-dimethyl-3R-(1',2'-dichloro-2',2'-dibromoethyl)-cyclopropane-1R-carboxylate Using the procedure of Example 1, the above acid was reacted with thionyl chloride in the presence of pyridine to obtain 2,2-dimethyl-3R(1',2'-dichloro-2',2'-dibromoethyl)-cyclopropane-1R-carboxylic acid chloride which was used as is.

Using the procedure of Example 1, the acid chloride was reacted with (R,S)α-cyano-3-phenoxy-benzyl alcohol in the presence of pyridine to obtain a mixture of the A and B isomers of (R,S)α-cyano-3-phenoxy-benzyl 2,2-dimethyl-3R-(1',2'-dichloro-2',2'-dibromoethyl)-cyclopropane-1R-carboxylate.

R.M.N. Spectrum

Peaks at 1.23–1.52 p.p.m. (hydrogen atoms of the methyls in the 2 position of the cyclopropane); peaks of 1.77–2.11 p.p.m. (hydrogen atoms in the 1 and 3 positions of the cyclopropane); peaks at 4.72–4.88 and at 5.02–5.21 p.p.m. (hydrogen atoms in the 1' position of the ethyl side chain in the 3 position of the cyclopropane); peaks of 6.40–6.43 p.p.m. (hydrogen atom carried by the same carbon atom as the C≡N); peaks of 6.94–7.66 p.p.m. (hydrogen atoms of the aromatic rings).

EXAMPLE 5

2,2-dimethyl-3S-(1',2'-dichloro-2',2'-dibromoethyl)-cyclopropane-1R-carboxylic acid A solution of 24 g of 2,2-dimethyl-3S-(2',2'-dibromovinyl)-cyclopropane-1R-carboxylic acid in 20 ml of carbon tetrachloride and 20 ml of methylene chloride was cooled to −10° C. and was saturated with chlorine while passing the reaction mixture over a refrigerant with a coolant at −60° C. (methanol-dry ice) to avoid loss of chlorine. The mixture was stirred for 2½ hours at −10° C. and then 90 minutes at 10° C. Excess chlorine was evaporated and the mixture was evaporated to dryness under reduced pressure. The 35.5 g of residue was chromatographed over silica gel and was eluted with a 75-25-1 cyclohexane-ethyl acetate-acetic acid mixture and then with an 80-20-1 mixture of the same solvents to obtain 16.3 g of 2,2-dimethyl-3S-(1',2'-dichloroethyl-2',2'-dibromoethyl)-cyclopropane-1R-carboxylic acid.

RMN Spectrum (deuterochloroform):

peaks at 1.33–1.56 ppm (hydrogens of geminal methyls of cyclopropane); at 1.70–2.25 ppm (1- and 3-hydrogens of cyclopropane); at 4.10–4.38 ppm (1'-hydrogen of 3-ethyl of cyclopropane); and at 10.9 ppm (carboxyl hydrogen).

(R,S)α-cyano-3-phenoxy-benzyl 2,2-dimethyl-3S-(1',2'-dichloro-2',2'-dibromoethyl)-cyclopropane-1R-carboxylate Using the procedure of Example 1, the above said was reacted with thionyl chloride to obtain 2,2-dimethyl-3S-(1',2'-dichloro-2',2'-dibromoethyl)-cyclopropane-1R-carboxylic acid chloride which was reacted with (R,S)α-cyano-3-phenoxy-benzyl alcohol to obtain a mixture of the A and B isomers of (R,S)α-cyano-3-phenoxy-benzyl 2,2-dimethyl-3S-(1',2'-dichloro-2',2'-dibromoethyl)-cyclopropane-1R-carboxylate.

RMN Spectrum:

peaks at 1.22–1.27–1.37–1.4–1.45 ppm (hydrogens of 2-methyls of cyclopropane); at 1.67 to 2.5 ppm (1- and 3-hydrogens of cyclopropane); at 3.67 to 4.5 ppm (1'-hydrogen of 3-ethyl of cyclopropane); at 6.52 ppm hydrogen (attached to same carbon as —CN); and at 7.0 to 7.67 ppm (hydrogens of aromatic ring).

EXAMPLE 6

2,2-dimethyl-3S-(1',2'-dibromo-2',2'-difluoroethyl)-cyclopropane-1R-carboxylic acid Using the procedure of Example 1, 2,2-dimethyl-3S-(2',2'-difluorovinyl)-cyclopropane-1R-carboxylic acid was reacted with bromine at −60° C. to obtain a mixture of the A and B isomers of 2,2-dimethyl-3S-(1',2'-dibromo-2',2'-difluoroethyl)-cyclopropane-1R-carboxylic acid melting at 122° C.

RMN Spectrum:

peaks at 1.33 to 1.36 ppm (hydrogens of 3-methyls of cyclopropane); at 1.60 to 2.23 ppm (1- and 3-hydrogens of cyclopropane); at 3.75 to 4.37 ppm (1'-hydrogen of 3-ethyl of cyclopropane); and at 10.96 ppm (carboxyl hydrogen).

(S) allethrolone 2,2-dimethyl-3S-(1',2'-dibromo-2',2'-difluoroethyl)-cyclopropane-1R-carboxylate Using the procedure of Example 1, the above acid was reacted with thionyl chloride to form 2,2-dimethyl-3S-(1',2'-dibromo-2',2'-difluoroethyl)-cyclopropane-1R-carboxylic acid chloride which was used as is and was reacted with (S) allethrolone in the presence of pyridine to obtain a mixture of the A and B isomers of (S) allethrolone 2,2-dimethyl-3S-(1',2'-dibromo-2',2'-difluoroethyl)-cyclopropane -1R-carboxylate.

RMN Spectrum:

peaks at 1.32 ppm (hydrogens of 2-methyls of cyclopropane); at 1.26 to 1.68 and 1.73 to 2.19 ppm (1-hydrogens of cyclopropane); at 1.20 ppm (hydrogens of 3-methyl of allethrolone), at 2.93 to 3.05 ppm (hydrogens of 1'-methylene of allyl chain); at 4.83 to 5.25 ppm (hydrogens of terminal methylene of allyl chain); at 3.58 to 4.33 ppm (1'-hydrogen of 3-ethyl of cyclopropane); peaks at 4.83 to 5.25 ppm (2'-hyrogen of allyl chain); and at 5.83 ppm (4-hydrogens of allethrolone).

EXAMPLE 7

2,2-dimethyl-3R-(1',2'-dibromo-2',2'-dichloroethyl)-cyclopropane-1R-carboxylic acid Using the procedure of Example 1, 2,2-dimethyl-3R-(2',2'-dichlorovinyl)-cyclopropane-1R-carboxylic acid was reacted with bromine to obtain a mixture of the A and B isomers of 2,2-dimethyl-3R-(1',2'-dibromo-2',2'-dichloroethyl)-cyclopropane-1R-carboxylic acid.

RMN Spectrum:

peaks at 1.26–1.30 and at 1.41–1.42 ppm (hydrogens of 3-methyls of cyclopropane); at 1.83–2.17 ppm (1- and 3-hydrogens of cyclopropane); at 4.83 to 5.58 ppm (1'-hydrogen of 3-ethyl of cyclopropane); and at 8.17 ppm (carboxyl hydrogen).

(R,S)α-cyano-3-phenoxy-benzyl 2,2-dimethyl-3R-(1',2'-dibromo-2',2'-dichloroethyl)-cyclopropane-1R-carboxylate Using the procedure of Example 1, the said acid was reacted with thionyl chloride to obtain 2,2-dimethyl-3R-(1',2'-dibromo-2',2'-dichloroethyl)-cyclopropane-1R-carboxylic acid chloride which was used as and was reacted with (R,S)α-cyano-3-phenoxy-benzyl alcohol to obtain a mixture of A and B isomers of (R,S)α-cyano- 3-phenoxy-benzyl 2,2-dimethyl-3R-(1',2'-dibromo-2',2'-dichloroethyl)-cyclopropane-1R-carboxylate.

EXAMPLE 8

2,2-dimethyl-3R-(1',2',2',2'-tetrachloroethyl)-cyclopropane-1R-carboxylic acid 11.8 g of chlorine were dissolved in 30 ml of carbon tetrachloride and then a solution of 16.7 g of 2,2-dimethyl-3R-(2',2'-dichlorovinyl)-cyclopropane-1R-carboxylic acid in 40 ml of methylene chloride was added thereto at 0° C. The mixture was stirred at 0° C. for 24 hours and then at 25° C. for 3 hours and the excess chlorine was removed by bubbling nitrogen through the mixture. The mixture was evaporated to dryness under reduced pressure and the residue was chromatographed over silica gel. Elution with an 8-2 cyclohexane-ethyl acetate mixture yielded a product which was crystallized from petroleum ether (b.p.=35°–75° C.) to obtain 3.14 g of 2,2-dimethyl-3R-(1',2',2',2'-tetrachloroethyl)-cyclopropane-1R-carboxylic acid melting at 144° C.

Analysis: $C_8H_{10}Cl_4O_2$; molecular weight =279.98 Calculated: %C 34.3; %H 3.6; %Cl 50.6; Found: 34.4; 3.7; 50.3.

RMN Spectrum (deuterochloroform):
peaks at 1.26–1.42 ppm and 1.30–1.42 ppm (hydrogens of geminal methyls); at 4.67–5.17 ppm and 5.08–5.43 ppm (1'-hydrogen of 3-ethyl of cyclopropane); at 1.67–2.00 ppm (1- and 3-hydrogens of cyclopropane); and at 10.2 ppm (carboxyl hydrogen).

3-phenoxy-benzyl 2,2-dimethyl-3R-(1',2',2',2'-tetrachloroethyl)-cyclopropane-1R-carboxylate A mixture of 6.75 g of the above product in 60 ml of petroleum ether (b.p.=35°–70° C.) and 8.7 ml of thionyl chloride was refluxed for 4½ hours and was then evaporated to dryness under reduced pressure. The residue was added to benzene and the solution was evaporated to dryness to obtain raw 2,2-dimethyl-3R-(1',2',2',2'-tetrachloroethyl)-cyclopropane-1R-carboxylic acid chloride which was used as and a solution of 5.2 g of 3-phenoxy-benzyl alcohol in 50 ml of benzene was added at 75° C. to a solution of the said acid chloride in 60 ml of benzene followed by the addition of 2.6 ml of pyridine and stirring for 16 hours at 20° C. The reaction mixture was poured into a water-hydrochloric acid mixture and the mixture was extracted with ethyl ether. The ether extracts were evaporated to dryness to obtain 11 g of residue which was chromatographed over silica gel. Elution with a 1-1 benzene-cyclohexane mixture and crystallization from ether gave a first fraction of 4.6 g of 3-phenoxy-benzyl 2,2-dimethyl-3R-(1',2',2',2'-tetrachloroethyl)-cyclopropane-1R-carboxylate with a melting point of 86° C. and a specific rotation of $[\alpha]_D^{20} = -86.5$ (c=0.5% in benzene).

Analysis: $C_{21}H_{20}Cl_4O_3$; molecular weight=462.20 Calculated: %C 54.56; %H 4.36; %Cl 30.68; Found: 54.9; 4.5; 30.3.

| U.V. Spectrum (ethanol): | |
|---|---|
| Inflex. towards 226 nm | $E_1^1 = 228$ |
| Inflex. towards 266 nm | $E_1^1 = 36$ |
| Max. at 271 nm | $E_1^1 = 41$ |
| Max. 277 nm | $E_1^1 = 40$ |

RMN Spectrum (deuterochloroform):
peaks at 1.27–1.4 ppm (hydrogens of geminal methyls of isomer A); at 5.13 ppm (hydrogens of

of isomer A); at 5.27–5.43 ppm (1'-hydrogen of 3-ethyl of isomer A); at 1.23–1.40 ppm (hydrogens of geminal methyls of isomer B); at 5.18 ppm (hydrogens of

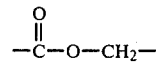

of isomer B); at 4.83–5.17 ppm (1'-hydrogen of 3-ethyl of isomer B); at 1.61–2.03 ppm (1- and 3-hydrogens of cyclopropane); and at 6.92–7.58 ppm (hydrogens of aromatic ring). The said spectrum showed that the product was about 90% of isomer A and about 10% of isomer B.

EXAMPLE 9

2,2-dimethyl-3S-(1',2',2',2'-tetrachloroethyl)-cyclopropane-1R-carboxylic acid

A solution of 18.8 g of 2,2-dimethyl-3S-(2',2'-dichlorovinyl)-cyclopropane-1R-carboxylic acid in 30 ml of methylene chloride was added over 15 minutes at −10° C. to a solution of 13.25 g of chlorine in 30 ml of carbon tetrachloride and the resulting mixture was passed over a refrigerant in which circulated a liquid at −60° C. to condense the nonreacted chlorine. The mixture was stirred at −10° C. for 90 minutes and then for 90 minutes at 0° C. and excess chlorine was removed at 20° C. by bubbling nitrogen therethrough. The mixture was evaporated to dryness under reduced pressure and the residue was chromatographed over silica gel. Elution with a 7-3 cyclohexane-ethyl acetate mixture to obtain 23 g of 2,2-dimethyl-3S-(1',2',2',2'-tetrachloroethyl)-cyclopropane-1R-carboxylic acid which was used as is for the next step.

R.M.N. Spectrum (deutero chloroform)
Peaks 1.25–1.53 p.p.m. characteristic of hydrogen atoms of the methyls in the 2 position of the cyclopropyle; peaks at 1.68–2.21 p.p.m. characteristic of hydrogen atoms in the 1 and 3 positions of the cyclopropyle; peaks 4.12–4.21 p.p.m. characteristic of the hydrogen atom in the 1' position of the substituted ethyl side chain; peak at 11.3 p.p.m. characteristic of the hydrogen of the carboxyl.

(R,S) α-cyano-3-phenoxy-benzyl 2,2-dimethyl-3S-(1',2',2',2'-tetrachloroethyl)-cyclopropane-1R-carboxylate 12.276 g of the said acid were added to a mixture of 30 ml of petroleum ether (b.p.=35°–75° C.) and 16 ml of thionyl chloride and the mixture was refluxed for 4½ hours and was then evaporated to dryness under reduced pressure. The residue was taken up in benzene and the solution was evaporated to dryness to obtain 2,2-dimethyl-3S-(1',2',2',2'-tetrachloroethyl)-cyclopropane-1R-carboxylic acid chloride which was used as is. A solution of 10.5 g of (R,S) α-cyano-3-phenoxy-benzyl alcohol in 20 ml of benzene was rapidly added at 5° C. to a mixture of the said acid chloride in 2 of benzene and 4.5 ml of pyridine were rapidly added there. The mixture was stirred at 20° C. for 16 hours and was poured into a mixture of ice-water-hydrochloric acid. The mixture was extracted with ethyl ether and the organic phase was washed with water, dried and evaporated to dryness under reduced pressure. The residue was chromatographed over silica gel and was eluted with a 9-1 cyclohexane-ethyl acetate mixture to obtain 14.18 g of (R,S) α-cyano-3-phenoxybenzyl 2,2-dimethyl-3S-(1',2',2',2'-tetrachloroethyl)-cyclopropane-1R-carboxylate with a specific rotation of $[\alpha]_D^{20} = -22.5°$ (c=0.5% in benzene).

Analysis: $C_{22}H_{19}Cl_4NO_3$; molecular weight=487.21 Calculated: %C 54.2; %H 3.9; %Cl 29.1; %N 2.9; Found: 54.0; 4.0; 29.0; 2.7.

I.R. Spectrum (chloroform):
Absorptions at 1742 cm$^{-1}$ (carbonyl) and at 1610, 1584 and 1484 cm$^{-1}$ (aromatic ring).

| U.V. Spectrum (ethanol): | |
|---|---|
| Inflex. at 230 nm | $E_1^1 = 230$ |
| Inflex. at 267 nm | $E_1^1 = 41$ |
| Inflex. at 271 nm | $E_1^1 = 44$ |
| Max. at 277 nm | $E_1^1 = 49$ |
| Inflex. at 283 nm | $E_1^1 = 37$ |
| Inflex. at 305 nm | $E_1^1 = 4$ |

RMN Spectrum (deuterochloroform):
peaks at 1.22–1.42 ppm (hydrogens of methyl); at 1.50–2.50 ppm (1- and 3-hydrogens of cyclopropane); at 3.66–4.41 ppm (1'-hydrogen at 3-ethyl of cylcopropane); at 6.5 ppm (hydrogen on same carbon as -CN); and at 7.00–7.66 ppm (hydrogens of aromatic ring).

EXAMPLE 10

2,2-dimethyl-3R-(1',2'-dibromo-2',2'-difluoroethyl)-cyclopropane-1R-carboxylic acid A solution of 15.2 g of bromine in 40 ml of carbon tetrachloride was added over 2 hours at −65° C. to a solution of 17 g of 2,2-dimethyl-3R-(2',2'-difluorovinyl)-cyclopropane-1R-carboxylic acid in 120 ml of methylene chloride and the mixture was stirred for 2½ hours at −65° C. after which the temperature was allowed to return to room temperature. The mixture was evaporated to dryness under reduced pressure and the residue was dissolved in 50 ml of hot carbon tetrachloride The solution was cooled to 0° C. and was stirred at 0° C. for 45 minutes and was then filtered. The filtrate was evaporated to dryness under reduced pressure and the residue was dissolved in 40 ml of carbon tetrachloride. The mixture was stirred at −10° C. for 30 minutes and was filtered. The filtrate was evaporated to dryness under reduced pressure and the residue was chromatographed over silica gel. Elution with a 3-1 cyclo hexane-ethyl acetate mixture yielded a product which was crystallized from petroleum ether (b.p.=35°-75° C.) to obtain 1.465 g of 2,2-dimethyl-3R-(1',2'-dibromo-2',2'-difluoroethyl)cyclopropane-1R-carboxylic acid melting at 124° C.

RMN Spectrum (deuterochloroform):
peaks at 1.28–1.38 ppm (hydrogens of geminal methyls); at 1.67–2.0 ppm (1- and 3-hydrogens of cyclopropane); and at 4.67–5.33 ppm (1'-hydrogen of 3-ethyl of cyclopropane).

(S) allethrolone 2,2-dimethyl-3R-(1',2'-dibromo-2',2'-difluoroethyl)-cyclopropane-1R-carboxylate A mixture of 2.5 ml of thionyl chloride, 1.43 g of the said acid and 15 ml of petroleum ether (b.p.=35°-75° C.) was refluxed for 4½ hours and then excess thionyl chloride was removed and the mixture was evaporated to dryness under reduced pressure. The residue was taken up in benzene and the solution was evaporated to dryness under reduced pressure to obtain 2,2-dimethyl-3R-(1',2'-dibromo-2',2'-difluoroethyl)cyclopropane-1R-carboxylic acid chloride which was used as is.

A solution of 0.7 g of (S) allethrolone in 5 ml of benzene was added at 2° C. to a solution of the product of Example 1 in 10 ml of benzene and after the addition of 0.5 ml of pyridine, the mixture was stirred for 16 hours at 20° C. The mixture was poured into a water-ice-hydrochloric acid mixture and the mixture was extracted with ethyl ether. The organic phase was washed with water, dried over sodium sulfate and evaporated to dryness to obtain 2.02 g of raw product. The latter was chromatographed over silica gel and was eluted with a 4-1 cyclohexane-ethyl acetate mixture to obtain 1.224 g of (S) allethrolone 2,2-dimethyl-3R-(1',2'-dibromo-2',2'-difluoroethyl)-cyclopropane-1R-carboxylate.

Analysis: $C_{17}H_{20}Br_2F_2O_3$; molecular weight=470.162 Calculated: %C 43.4; %H 4.3; %Br 34.0; %F 8.1; Found: 43.2; 4.4; 33.7; 8.1.

| U.V. Spectrum (ethanol): | |
|---|---|
| Max. at 227–228 nm | $E_1^1 = 348$ |

RMN Spectrum (deuterochloroform):
peaks at 1.25–1.36 ppm (hydrogens of geminal methyls); at 2.02–2.06 ppm (hydrogens of 2-methyl of allethrolone); at 4.83–5.25 ppm (hydrogens of terminal methylene of allyl of allethrolone); at 5.5 to 6.17 ppm (hydrogen β to lateral chain of allethrolone and hydrogen of 1-carbon of ellethrolone); at 4.83–6.17 ppm (1'-hydrogen of 3-ethyl of cyclopropane); at 1.67–2.16 ppm (1- and 3-hydrogens of cyclopropane); at 2.95–3.05 ppm (hydrogens of methylene α- to side chain of allethrolone); and at 1.67–3.17 ppm (methylene of allethrolone ring).

EXAMPLE 11

2,2-dimethyl-3R-(1',2'-dibromo-2'-(R,S)-fluoro-2'-chloroethyl)-cyclopropane-1R-carboxylic acid A solution of 2.4 ml of bromine in 20 ml of carbon tetrachloride was added at −10° C. over 30 minutes to a solution of 8.9 g of a mixture of the E and Z isomers of 2,2-dimethyl-3R-(2'-chloro-2'-fluorovinyl)-cyclopropane-1R-carboxylic acid in 100 ml of carbon tetrachloride and the mixture was stirred at 10° C. for 4 hours. The mixture was evaporated to dryness under reduced pressure and the residue was chromatographed over silica gel. Elution with ethyl acetate yielded 13.7 g of 2,2-dimethyl-3R-(1',2'-dibromo-2'-(R,S)-fluoro-2'-chloroethyl)-cyclopropane-1R-carboxylic acid.

I.R. Spectrum (chloroform):
Absorption at 1710 cm$^{-1}$ (carbonyl) and 3510 cm$^{-1}$ (OH).

RMN Spectrum (deuterochloroform):
peaks at 1.30–1.32–1.42 ppm (hydrogens of geminal methyls); at 1.75–2.08 ppm (1- and 3-hydrogens of cyclopropane); at 4.67–5.50 ppm (1'-hydrogen of 3-ethyl of cyclopropane); and at 10.75 ppm (carboxyl hydrogen).

3-phenoxy-benzyl 2,2-dimethyl-3R-(1',2'-dibromo-2'-(R,S)-fluoro-2'-chloroethyl)-cyclopropane-1R-carboxylate A mixture of 3.5 g of the acid of Example 1, 3.5 g of 3-phenoxy-benzyl alcohol, 3.5 g of neopentyl acetal of dimethylformamide and 35 ml of benzene was heated for 17 hours at 50° C. and was then cooled and evaporated to dryness under reduced pressure. The residue was chromatographed over silica gel and was eluted with a 1-1 benzene-cyclohexane mixture to obtain 1.050 g of the A isomer of 3-phenoxy-benzyl 2,2-dimethyl-3R-(1',2'-dibromo-2'-(R,S)-fluoro-2'-chloroethyl)-cyclopropane-1R-carboxylate melting at 50° C.

Analysis: $C_{21}H_{20}Br_2ClFO_3$; molecular weight=534.65 Calculated: %C 47.17; %H 3.77; %Br 29.89; %Cl 6.63; %F 3.55; Found: 47.4; 3.8; 29.4; 7.2; 3.7.

I.R. Spectrum (chloroform):

Absorption at 1735 cm$^{-1}$ (carbonyl) and 1675, 1590 and 1490 cm$^{-1}$ (aromatic ring).

RMN (Spectrum (deuterochloroform):

peaks at 1.23–1.39 ppm (hydrogens of geminal methyls); at 1.73–2.01 ppm (1- and 3-hydrogens of cyclopropane); at 5.08 ppm (hydrogens of methylene of benzyl); at 5.08–5.50 ppm (1'-hydrogen of 3-ethyl of cyclopropane); and at 6.83–7.58 (hydrogens of aromatic ring).

Also recovered were 0.62 g of the B isomer of the same ester having the following charactertics:

Analysis: Calculated: %C 47.17; %H 3.77; %Cl 6.03; %F 3.55; %Br 29.89; Found: 47.5; 3.8; 6.2; 3.6; 29.6.

I.R. Spectrum (chloroform): identical to that of isomer A. RMN Spectrum (deuterochloroform):

peaks at 1.22–1.34 ppm (hydrogens of geminal methyls); at 1.75–2.0 ppm (1- and 3-hydrogens of cyclopropane); at 5.12 ppm (hydrogens of methylene of benzyl); at 4.83–5.33 ppm (1'-hydrogen of 3-ethyl of cyclopropane); and at 5.83–7.5 ppm (hydrogens of aromatic ring).

The starting acid was prepared by the procedure of Brown [thesis of 1974 entitled Structure Activity Studies of Halopyrethroids published in 1976 by Xerox University Microfilms, Ann Arbor., Michigan, p. 27 to 29]. to make the corresponding dl-trans acid but using tert.-butyl 2,2-dimethyl-3S-formyl-cyclopropane-1R-carboxylate in place of tert.-butyl 2,2-dimethyl-3RS-formyl-cyclopropane-1RS-carboxylate.

EXAMPLE 12

A wettable powder was prepared containing 20 g of 2,2-dimethyl-3R-(1',2',2',2'-tetrachloroethyl)-cyclopropane-1R-carboxylic acid [compound E], 15 g of Ekapersol (condensation product of sodium naphthalene sulfonate), 0.5 g of Brecolane NVA (sodium alkyl naphthalene sulfonate), 32.5 g of Zeosil 39 (synthetic precipitated hydrated silica) and 25 g of Vercoryl S (colloidal kaolin).

EXAMPLE 13

An antifungal composition was prepared as a solution containing 25 g/l of 2,2-dimethyl-3R-(1',2',2',2'-tetrachloroethyl)-cyclopropane-1R-carboxylic acid, 80 g/l of Emcol H 300 B [calcium salt of alkyl benzene sulfonates admixed with polyoxyethylene ethers] and 895 g/l of xylene.

EXAMPLE 14

A biocidal composition in the form of a wettable powder was prepared containing 25 g of 2,2-dimethyl-3S-(1',2',2',2'-tetrabromoethyl)-cyclopropane-1R-carboxylic acid, 15 g of Ekapersol S, 0.5 g of Brecolane NVA, 34.5 g of Zeosil 39 and 25 g of Vercoryl S. A biocidal solution was prepared from 25 g of 2,2-dimethyl-3S-(1',2',2',2'-tetrabromoethyl)-cyclopropane-1R-carboxylic acid dissolved in 75 g of ethanol.

ANTIFUNGAL ACTIVITY

The antifungal tests were effected with 2,2-dimethyl-3R-(1',2'-dichloro-2',2'-dibromoethyl)-cyclopropane-1R-carboxylic acid [product A], 2,2-dimethyl-3S-(1',2'-dibromo-2',2'-difluoroethyl)-cyclopropane-1R-carboxylic acid [product B], 2,2-dimethyl-3R-(1',2'-dibromo-2',2'-dichloroethyl)-cyclopropane-1R-carboxylic acid [product C], 2,2-dimethyl-3S-(1',2',2',2'-tetrabromoethyl)-cyclopropane-1R-carboxylic acid [product D], 2,2-dimethyl-3R-(1',2',2',2'-tetrachloroethyl)-cyclopropane-1R-carboxylic acid [product E], 2,2-dimethyl-3R-(1',2',2',2'-tetrabromoethyl)-cyclopropane-1R-carboxylic acid [product F] and 2,2-dimethyl-3S-(1',2'-dibromo-2',2'-dichloroethyl)-cyclopropane-1R-carboxylic acid [product G].

The fungiostatic efficacy of the test compounds was determined by introducing 0.5 ml of a solution of the compound and 0.5 ml of spores of the fungus to be combatted adjusted to about 100,000 spores per ml into 4 ml of Staron nutritive medium and after 7 days of incubation, readings were taken by visual observation of the development of the fungus or the absence of development (0 to 100% efficacy). The Staron nutritive media consisted of 20 g of glucose, 6 g of peptone, 1 g of yeast extract, 4 g of corn steep, 0.5 g of sodium chloride, 1 g of monopotassium phosphate, 0.5 g of magnesium sulfate, 10 mg of ferrous sulfate and sufficient water for a final volume of one liter. The results are reported in Table I.

TABLE I

| Fungus | Compound | Fungistatic efficacy in ppm |
| --- | --- | --- |
| Botrytis Cinerea | A | between 150 to 200 |
|  | E | between 75 to 100 |
|  | A | between 100 to 150 |
| Fusarium Roseum | C | between 100 to 150 |
|  | D | between 75 to 100 |
|  | E | between 50 to 75 |
|  | G | between 100 to 150 |
| Phoma species | A | between 50 to 75 |
|  | B | between 100 to 150 |
|  | C | between 150 to 200 |
|  | D | between 100 to 150 |
|  | E | between 50 to 75 |
|  | G | between 100 to 150 |
| Penicillium Roqueforti | A | between 50 to 75 |
|  | B | between 100 to 150 |
|  | C | between 150 to 200 |
|  | D | between 100 to 150 |
|  | E | between 50 to 75 |
|  | G | between 100 to 150 |

The results of Table I show that the tested compounds have an interesting antifungal activity.

BIOCIDAL ACTIVITY

This test was effected with glue using a solution of 3 g of carboxymethyl starch in 91 g of water and the test compound was added thereto in the form of a solution in 1 ml of acetone. 5 ml of an inoculum constituted of a mixture of spores of *Aerobacter-Aerogenes, Pseudomonas Aeruginosa, Escherichia coli, Serratia Marceseens, Bacillus substilis* and *Staphylococcus Aureus* were added thereto and the mixture was heated at 37° C. for 48 hours and was then held at 20° C. for 6 days The control of the bacterial population was determined 48 hours and 8 days after treatment and contamination by the serum dilution method and incorporated into bouillon agar. The results are reported in Table II.

TABLE II

| Compound | Population (Colonies/ml) After treatment and infestation | | | | | % Mortality (Compared to Controls) After treatment and infestation | | | | |
|---|---|---|---|---|---|---|---|---|---|---|
| | 48 Hours | | | 8 Days | | | 48 Hours | | 8 Days | |
| | 0.05% | 0.025% | Untreated | 0.05% | 0.025% | Untreated | 0.05% | 0.025% | 0.05% | 0.025% |
| A | 0 | $12 \times 10^6$ | $57 \times 10^6$ | 0 | $15 \times 10^6$ | $17 \times 10^7$ | 100 | 78.947 | 100 | 91.176 |
| B | 0 | 0 | $57 \times 10^6$ | 0 | 0 | $17 \times 10^7$ | 100 | 100 | 100 | 100 |
| C | 0 | $12 \times 10^4$ | $57 \times 10^6$ | 0 | $16 \times 10^5$ | $17 \times 10^7$ | 100 | 99.789 | 100 | 99.059 |
| D | 0 | 0 | $73 \times 10^6$ | 0 | 630 | $17 \times 10^6$ | 100 | 100 | 100 | 99.996 |
| E | 0 | $30 \times 10^5$ | $57 \times 10^6$ | 0 | $12 \times 10^6$ | $17 \times 10^7$ | 100 | 94.737 | 100 | 92.941 |
| F | 300 | $87 \times 10^5$ | $85 \times 10^6$ | 270 | $21 \times 10^6$ | $73 \times 10^6$ | 99.999 | 89.764 | 99.999 | 71.233 |
| G | 0 | $47 \times 10^4$ | $44 \times 10^6$ | 0 | $51 \times 10^6$ | $54 \times 10^6$ | 100 | 98.932 | 100 | 95.555 |

The results of Table II show that the tested compounds have an interesting biocidal activity.

Various modifications of the products and methods of the invention may be made without departing from the spirit or scope thereof and it is to be understood that the invention is intended to be limited only as defined in the appended claims.

We claim:

1. A compound of the formula

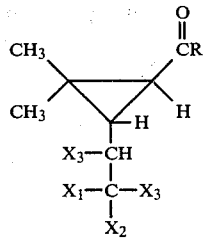

wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is halogen; in any of the possible diastereoisomeric forms.

2. A compound of claim 1 in its diastereoisomers or mixtures thereof selected from the group consisting of 2,2-dimethyl-3S-(1',2',2',2'-tetrabromoethyl)-cyclopropane-1R-carboxylic acid chloride, 2,2-dimethyl-3S-(1',2'-dibromo-2',2'-dichloroethyl)-cyclopropane-1R-carboxylic acid chloride, 2,2-dimethyl-3R-(1',2'-dichloro-2',2'-dibromoethyl)cyclopropane-1R-carboxylic acid chloride, 2,2-dimethyl-3S-(1',2'-dichloro-2',2'-dibromoethyl)-cyclopropane-1R-carboxylic acid chloride and 2,2-dimethyl-3S-(1',2'-dibromo-2',2'-difluoroethyl)-cyclopropane-1R-carboxylic acid chloride.

3. A compound of claim 1 in the form of its diastereoisomers or mixtures thereof which is 2,2-dimethyl-3R-(1',2',2',2'-tetrabromoethyl)-cyclopropane-1R-carboxylic acid chloride.

4. A compound of claim 1 in the form of its diastereoisomers or mixtures thereof which is 2,2-dimethyl-3R-(1',2'-dibromo-2',2'-dichloroethyl)-cyclopropane-1R-carboxylic acid chloride.

5. A compound of claim 1 in the form of diastereoisomers or mixtures thereof which is 2,2-dimethyl-3S-(1',2',2',2'-tetrachloroethyl)-cyclopropane-1R-carboxylic acid chloride.

6. A compound of claim 1 in the form of its diastereoisomers or mixtures thereof which is 2,2-dimethyl-3R-(1',2',2',2'-tetrachloroethyl)-cyclopropane-1R-carboxylic acid chloride.

7. A compound of claim 1 in the form of its diastereoisomers or mixtures thereof which is 2,2-dimethyl-3R-(1',2'-dibromo-2',2'-difluoroethyl)-cyclopropane-1R-carboxylic acid chloride.

8. A compound of claim 1 in the form of its diastereosiomers or mixtures thereof which is 2,2-dimethyl-3R-(1',2'-dibromo-2'-chloro-2'(RS) fluoroethyl)-cyclopropane-1R-carboxylic acid chloride.

* * * * *